United States Patent [19]

Shirley et al.

[11] Patent Number: 4,525,645
[45] Date of Patent: Jun. 25, 1985

[54] CYLINDRICAL BENDER-TYPE VIBRATION TRANSDUCER

[75] Inventors: Donald J. Shirley, Boerne; Thomas E. Owen, Helotes, both of Tex.

[73] Assignee: Southwest Research Institute, San Antonio, Tex.

[21] Appl. No.: 540,288

[22] Filed: Oct. 11, 1983

[51] Int. Cl.³ .............................................. H01L 41/08
[52] U.S. Cl. .................................. 310/337; 310/369; 367/159
[58] Field of Search ............... 310/331, 369, 337, 328; 367/159–161

[56] References Cited

U.S. PATENT DOCUMENTS

| | | | |
|---|---|---|---|
| 3,027,540 | 3/1962 | Howatt | 310/369 X |
| 3,068,446 | 12/1962 | Ehrlich | 310/369 X |
| 3,177,382 | 4/1965 | Green | 310/337 X |
| 3,215,078 | 11/1965 | Stec | 310/328 X |
| 3,389,274 | 6/1968 | Robertson | 310/328 |
| 3,706,967 | 12/1972 | Renna, Jr. | 310/337 |
| 3,845,333 | 10/1974 | Holloway | 310/337 X |
| 3,857,049 | 12/1974 | Zoltan | 310/328 |
| 4,135,109 | 1/1979 | Gingerich et al. | 310/369 X |
| 4,220,887 | 9/1980 | Kompanek | 310/369 X |
| 4,395,719 | 7/1983 | Majewski et al. | 310/369 X |

FOREIGN PATENT DOCUMENTS 2650356 11/1978 Fed. Rep. of Germany ...... 310/369

Primary Examiner—Mark O. Budd
Attorney, Agent, or Firm—Gunn, Lee & Jackson

[57] ABSTRACT

An acoustic transducer with high sensitivity and low resonance frequency is constructed of a cylinder having inner and outer layers rigidly bonded together. At least one layer is a thickness poled piezoelectric material. The cylinderical can be closed by end caps to shift nodal locations.

15 Claims, 9 Drawing Figures

CYLINDRICAL BENDER-TYPE VIBRATION TRANSDUCER

This invention was made under United States Government Contract No. H0212006 and the United States Government has a nonexclusive, nontransferable, irrevocable, paid-up license to practice or have practiced for or on behalf of the United States, this invention throughout the world.

BACKGROUND OF THE INVENTION

The present invention relates to electromechanical transducers and, more particularly, to a cylindrical bender-type vibration transducer. The present invention includes a hollow cylinder having two layers bonded together, i.e., a cylinder within a cylinder. At least one of the cylinders is made from a piezoelectric material polarized in the thickness direction. By use of the cylinder within a cylinder, there is essentially no vibration in the longitudinal direction along the cylinder axis and symmetric vibrations are received or transmitted radially with respect to the cylindrical axis. This type of configuration allows for greater sensitivity. Also, the mechanical resonance frequency may be lower than conventional cylindrical piezoelectric devices of a similar length and diameter. The use of the two cylindrical components allows the same mechanical resonance frequency of the bender design to be specified for various cylinder sizes.

In an alternative embodiment utilizing a barrel stave type of arrangement, the operation of a transducer may be shifted and/or controlled by the manner of electrical connection to, or excitation of, the piezoelectric elements within the transducer.

Also by adding end caps, the node of vibration is changed, causing the resonance frequency to decrease.

BRIEF DESCRIPTION OF THE PRIOR ART

Electromechanical transducers operating on piezoelectric principles have been used in many forms for many years. Bimorphic transducers consist of two separate plates or layers of piezoelectric material. The two layers are physically arranged and electrically excited so that one layer expands while the other layer contracts. The result is to produce counteracting stresses in the material, which causes the composite structure to bend. The same action can be obtained to a lesser degree if a single layer of piezoelectric material is bonded to a nonpiezoelectric plate or layer. Composite transducers of this type are commonly referred to as flat plate bender transducers. Some of the more common configurations of bender transducers include: (1) long rectangular plates that bend in the length mode; (2) square plates in which the center moves relative to the four corners; and (3) circular plates in which the center moves relative to the peripheral edge. All of these configurations have a planar structure.

Piezoelectric cylinders in a monopole configuration have been used in the past as illustrated by U.S. Pat. No. 4,347,539 to Trott. However, Trott does not use the dual layer cylinder as described by the present invention; therefore, there will be expansions and contractions in the longitudinal direction as is not possible by the present invention. Also, the increased sensitivity and matching of impedance is not possible with the Trott invention as is in the present invention.

Other types of cylindrical bender transducers may be illustrated by U.S. Pat. No. 2,614,143 to Williams. However, the cylindrical bender design of Williams has asymmetric bending, i.e., the axis of the cylinder bends. Further, Williams does not show the dual cylinder configuration as shown in the present invention. All that is shown in Williams is electrodes on the inside and outside of an electromechanical transducer.

Another cylindrical bender transducer is shown in U.S. Pat. No. 3,167,1623 to Petermann; however, Petermann does not refer to a layered bimorphic configuration. Further, Petermann does not provide symmetrical vibrations as is illustrated in FIG. 6 of Petermann.

While U.S. Pat. No. 3,447,217 to Kumada does cover bimorphic transducers, it does not have a cylindrical bimorphic transducer which provides symmetrical vibrations. Symmetrical vibrations radially transmitted or received about the cylinder axis are inherent in the present invention.

Perhaps U.S. Pat. No. 4,220,887 to Kompanek is the closest prior art known by applicant because it does provide for a generally cylindrical layered transducer, but the longitudinal slit prevents symmetrical vibrations. Further, the bands 20 limit vibration of the transducer radially, which is the primary mode of operation of the present invention.

None of the patents found by the applicant, the more relevant ones being cited hereinabove, address or disclose the idea of a cylindrical double wall transducer operating in the bender mode. Further, none of the references found shows symmetrical vibrations about the axis of the cylinder.

SUMMARY OF THE INVENTION

It is an object of the present invention to provide a cylindrical bender-type vibration transducer.

It is another object of the present invention to provide a piezoelectric electromechanical transducer formed from a two layered cylinder with at least one of the layers being made from a piezoelectric material polarized in the thickness direction and having electrodes bonded to the inner and outer faces of the piezoelectric material for either receiving or transmitting electrical signals.

It is yet another object of the present invention to provide a cylindrical bender-type vibration transducer of a cylindrical shape having an inner and outer layer bonded together. At least one of the layers is a piezoelectric ceramic material polarized in the thickness direction. The piezoelectric material has electrodes bonded to the inner and outer faces for either transmitting from or sending signals to the piezoelectric material. The transducer only vibrates in a radial direction about the cylindrical axis to provide symmetrical type vibrations.

An alternative embodiment of the cylindrical bender-type transducer includes placing end caps on each end of the transducer. The placing of end caps on each end of the transducer moves the vibrating nodes from approximately one-quarter of the length of the cylinder measured from each end thereof to essentially each end of the cylinder.

In another alternative embodiment, the outer cylinder could be metal or other non-piezoelectric solid material. The outer cylinder prevents the polarized internal piezoelectric material from vibrating along its longitudinal axis because rigid bonding between the two cylinders transforms the longitudinal motions into flexural motions. The inner and outer cylinders cancel out vibrations along the longitudinal axis.

The advantage of this method of construction over other methods of constructing cylindrical type acoustical transducers is that the bender mode of operation produces a transducer with higher sensitivity and a lower resonance frequency in a relatively small physical size device.

The basic concepts of the present invention envision a composite hollow cylinder with the walls being formed from two layers of material. One layer of the walls for the hollow cylinder consist of a piezoelectric ceramic material polarized in the thickness direction. The piezoelectric ceramic layer has metal electrodes bonded to the inside and outside faces. The second layer is rigidly bonded to the piezoelectric ceramic layer. The second layer can consist of an inert material, such as metal, an unpolarized ceramic, or active piezoelectric ceramic appropriately polarized and electroded for proper counteracting force or generative output relative to the first layer.

When used as a source transducer, an electric signal of appropriate magnitude and frequency is connected to the electrodes of the active piezoelectric ceramic layer (or two piezoelectric ceramic layers, if two are used) in such a way as to excite the two layers, causing the composite cylinder to radially expand and contract. When used as a receiver, the acoustical signal being detected applies a pressure wave or other form of vibratory excitation to the exterior of the cylinder causing the cylinder to mechanically expand and contract in response to the applied excitation. The expansion and contraction of the cylinder produces a corresponding electrical signal, which is available at the electrodes of the piezoelectric ceramic layer or layers. Rigid end caps may be applied to the ends of the cylinder to restrict the motion at the ends thereof and thereby increase the motion at the center of the cylinder.

The length, wall thickness and diameter of the cylinder and its two layers will affect the operating frequency range and sensitivity of the transducer. The two cylinders are rigidly bonded together with a material, such as an epoxy adhesive or other suitable cement.

If the two layers both consist of active polarized piezoelectric ceramic material with electroded inner and outer surfaces, a silver filled epoxy could be used to insure good electrical connection between the adjacent layers of the two cylinders. In such case, polarization of the piezoelectric ceramic cylinders can be in opposite directions requiring a series electrical connection, which is more suited for operation as a receiver transducer. If the two piezoelectric ceramic cylinders are polarized in the same direction, the piezoelectric ceramic cylinders require a parallel electrical connection which operates best as a source transducer.

If the outer cylinder is made from an inactive material, such as metal, the metal cylinder provides excellent shielding from external electrical fields and provides a rugged mechanical assembly. This is especially true if end caps are used that are also metal and are electrically connected with the outer cylinder.

In another alternative embodiment, either or both layers of piezoelectric ceramic material may be segmented in a manner similar to barrel staves with each of the segments having its own electrodes. If the electrodes of the segments are connected in series, the electrical output voltage of the transducer is increased in response to a given external pressure. Also in the segmented configuration, if the electrodes for the segments are connected in parallel, the device operates better as a source transducer by giving larger magnitude of acoustical vibrations per volt of electrical excitation.

By use of the segmented configuration, a multi-section cylindrical bender-type vibration transducer can be built to form a long cylindrical transducer. This overcomes prior difficulties in constructing and polarizing long thin piezoelectric ceramic elements having dimensions over about six inches in length. Each active section of a long cylindrical structure can be formed by segments arrayed about the cylindrical axis. These sections can be arrayed in ordered rows or staggered to eliminate any axial vibration modes. A cylindrical bender of any length can be constructed in sections without the requirement for using full length active ceramic segment elements.

In another alternative embodiment, a series of separate cylindrical bender transducers can be arranged along the common axis in such a manner as to pump incompressible liquids. By sizing inlet and outlet orifices, and exciting a series of the cylindrical bender-type transducers in a timed cascade arrangement, their contractions and dilations can result in a pumping action typically referred to as a peristaltic action. Basically as a wave motion starts down a series of cylindrical bender-type transducers, each of the transducers in series is timed to continue the wave the entire length thereof. One of the purposes of such a device is to provide an impellerless or pistonless pump that has a minimum contact with the fluid being pumped. This is particularly important in processing biological fluids, such as blood.

DESCRIPTION OF THE PREFERRED EMBODIMENT

Figure 1:
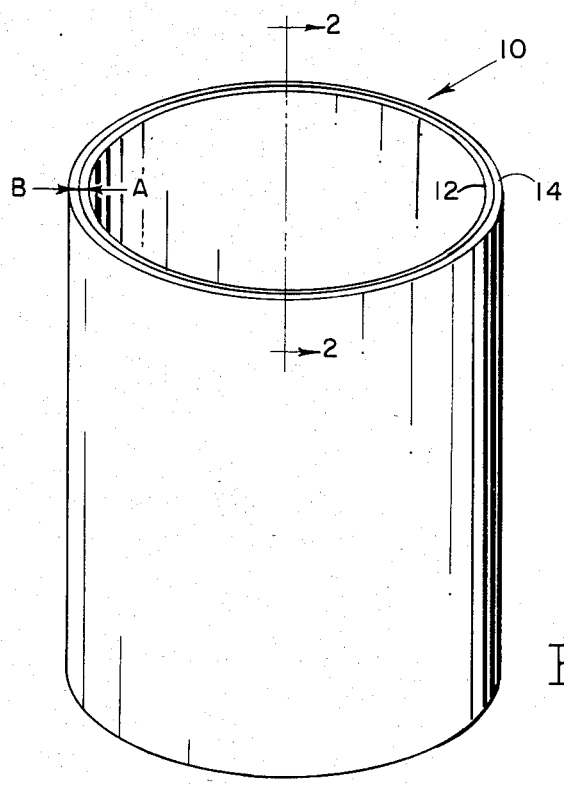
FIG. 1 is a perspective view of a cylindrical bender-type vibration transducer.

Referring to FIG. 1, there is pictorially illustrated a cylindrical bender-type vibration transducer represented generally by the reference numeral 10. The cylinder 10 consists of two layers 12 and 14 with the inside layer 12 being bonded to the outside layer 14 to form one integral cylinder 10. In the embodiment as shown in FIG. 1, both layers 12 and 14 are made from a piezoelectric ceramic material and are oppositely polarized in the thickness direction as represented by arrows A and B, respectively.

Figure 3:
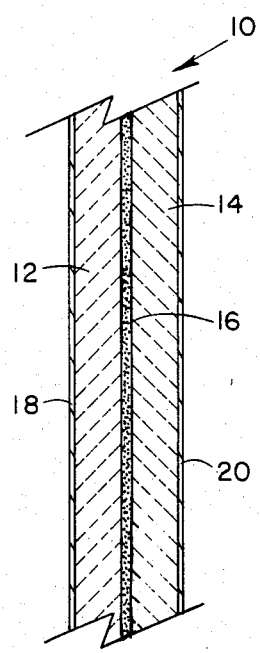
FIG. 3 is an enlarged sectional view of a part of the cylindrical wall shown in FIG. 2.
Figure 2:
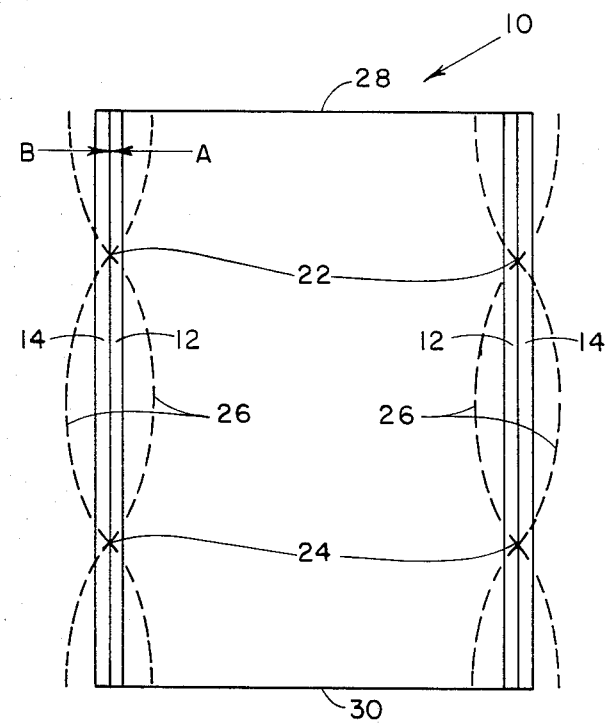
FIG. 2 is a cross-sectional view of FIG. 1 along section lines 2—2 illustrating in broken lines the vibration of the cylindrical walls.

A cross-sectional view of FIG. 1 is shown in FIG. 2. A better understanding of the construction of the cylindrical bender-type vibration transducer 10 as shown in FIG. 1 in a perspective view, and in a cross-sectional view in FIG. 2, can be obtained by a review of the enlarged cross-sectional view of a portion of the cylinder wall as shown in FIG. 3. The inner piezoelectric ceramic layer 12 is bonded to the outer piezoelectric ceramic layer 14 by a suitable bonding agent 16. The bonding agent 16 can be an epoxy adhesive or other suitable cement. A silver filled epoxy is suggested to insure good electrical connection between the adjacent surfaces of the layers 12 and 14. Electrodes 18 and 20 are electro-deposited on the inner and outer surfaces of the cylinder walls of the cylindrical transducer 10 as illustrated in FIG. 3. The electrodes 18 and 20 are made of suitable conductive material to either transmit or receive electrical signals to or from the piezoelectric ceramic layers 12 and 14. Neither the bonding agent 16 nor the electrodes 18 or 20 are of significant thickness to interfere with the vibrations of the cylindrical transducer 10. Because the thickness of the layers of the bonding agent 16 and electrodes 18 and 20 is so small, they have not been illustrated in FIGS. 1 and 2, and the thickness has been exaggerated for illustration purposes.

Referring to FIG. 2 in combination with FIG. 3, if an electrical signal of suitable magnitude and frequency is applied to electrodes 18 and 20, the cylindrical walls will vibrate by contractions and dilations about nodes 22 and 24. The contractions and dilations are illustrated by broken lines 26. The location of nodes 22 and 24 are located approximately one-quarter of the distance from the respective ends 28 and 30 of the cylindrical transducer 10. In actual practice, the location of the nodes 22 and 24 may be a percent or two less than one-quarter the distance from the respective ends 28 and 30, respectively.

The cylindrical bender-type vibration transducer 10 just described in connection with FIGS. 1–3 is an acoustical transducer capable of being used either as a generator or detector of acoustical waves in a fluid medium. The two layers 12 and 14 are constructed such that layer 12 is assembled in close fitting proximity with layer 14 and is of equal or slightly shorter length. The length, wall thickness, and diameter of the cylindrical transducer 10 affects the operating frequency range and sensitivity of the transducer 10.

Polarization of the ceramic cylinder can either be in opposite directions as illustrated in FIGS. 1 and 2 or in the same direction. If polarization is in the opposite direction, electrical connection is made to the inside electrode 18 of layer 12 and to the outside electrode 20 of layer 14. (See FIG. 3.) If polarization is in the same direction, one electrical connection is made to electrode 18 and electrode 20, and the other electrical connection is made to an electrode (not shown) contained in the bonding agent 16. In the first case of opposite directions of polarization, the connection to the cylindrical transducer 10 can be represented by a series electrical connection. In the second case of polarization in the same direction, the electrical connections can be represented by parallel electrical connection.

Figure 4:
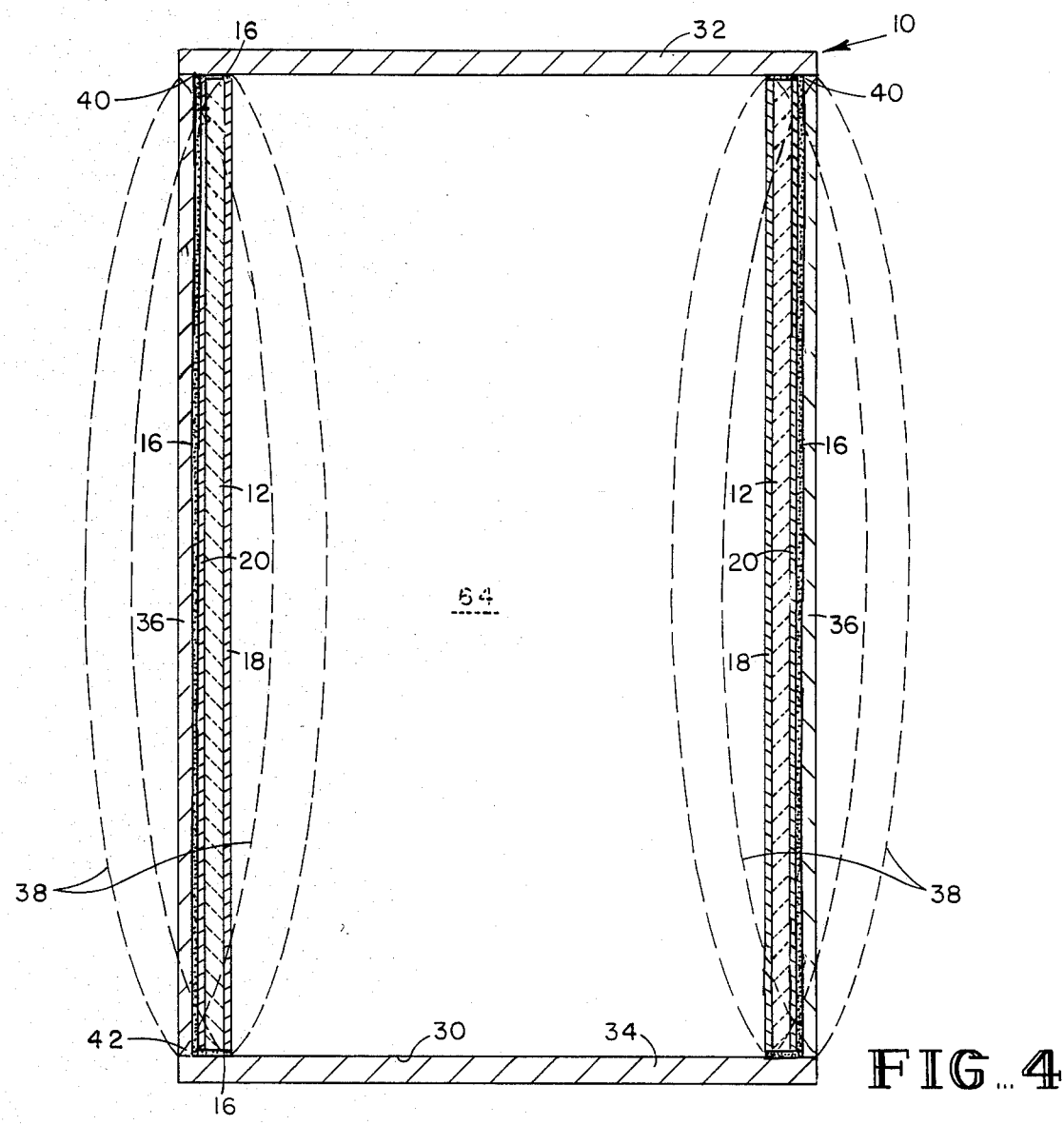
FIG. 4 is a cross-sectional view of an alternative embodiment of a cylindrical bender-type vibration transducer with broken lines representing vibrations of the cylindrical walls.

In an alternative embodiment, either layer 12 or 14 can be replaced by an inactive material, such as metal, unpolarized ceramic or glass. One of the more desired embodiments is when the outer layer 14 is replaced by a metal cylinder which can provide shielding from external stray electrical fields, and also provide for rugged mechanical assembly. This is particularly true if end caps 32 and 34 are placed on each end 28 and 30, respectively, of the cylindrical bender-type vibration transducer 10 as shown in FIG. 4. Particularly note that layer 14 previously explained in connection with FIGS. 1–3 has been replaced by layer 36 of a metallic material. FIG. 4 also represents the expansions and contractions of the cylindrical walls as pictorially represented by broken lines 38 if end caps 32 and 34 are attached to the cylindrical bender-type vibration transducer 10. It should be realized that the broken lines 38 (and also the broken lines 26 of FIG. 2) are exaggerations of the motion of the cylindrical walls for illustration purposes.

The location of the end caps 32 and 34 on each end 28 and 30, respectively, of the cylindrical bender-type vibration transducer 10 moves the nodes 22 and 24 of vibration as illustrated in FIG. 2, to immediately adjacent to the end caps 32 and 34 with the new nodes being represented by numerals 40 and 42, respectively. As can be seen by comparing FIG. 2 with FIG. 4, the magnitude of the expansion and contraction in a radial direction with respect to the axis of the cylindrical transducer 10 is increased by the use of end caps 32 and 34. In either embodiment as shown in FIGS. 1–3 or in FIG. 4, there are essentially no lengthwise vibrations along the axis of the cylindrical transducer 10. The flexural bending caused by the piezoelectric forces in respective layers 12 and 14 (or layers 12 and 36 in FIG. 4) tend to produce predominantly radial expansion and contraction of the cylinder.

By changing the piezoelectric ceramic layer 14 to a metallic layer 36 as is shown in FIG. 4, the resonance frequency of the cylindrical transducer 10 is decreased because of the lower rigidity of the metal. This is assuming that the layers 14 and 36 would have equal thickness. In a typical embodiment used by applicants, the layer 36 had approximately 64/1000 inch thickness and layer 12 had approximately 50/1000 inch thickness. The thickness of the bonding agent 16 and the thickness of the electrodes 18 and 20 is negligible. In an embodiment used by applicant, the diameter of the cylindrical bender-type vibration transducer was approximately two inches and the length approximately four inches. Using those dimensions, the resonant frequency was 18 kilohertz.

In a typical arrangement such as FIG. 1, the use of two piezoelectric cylinders of the same thickness (such as layers 12 and 14) would have a higher resonance frequency than the use of the piezoelectric cylinder and a metallic cylinder of the same thickness (such as layers 12 and 36) illustrated in FIG. 4. The adding of end caps 32 and 34 lowers the resonance frequency.

To have a good electrically shielded cylindrical bender-type vibration transducer 10, the end caps 32 and 34 as shown in FIG. 4 should be in electrical contact with the metallic layer 36. Also, the piezoelectric ceramic layer 12 should be slightly shorter so that electrical contact is not made with the end caps 32 and 34. Further, the bonding agent 16, which would be located between layers 12 and 36 of FIG. 4, should be of a nonconductive material. The bonding agent 16 may also extend between the ends of layer 12 and end caps 32 and 34 to insure electrical insultation. Electrodes 18 and 20 would be electro-deposited on both sides of layer 12, but neither electrode 18 or 20 would be in electrical contact with any of the metal of either layer 36 or end caps 32 and 34. Obviously, a suitable connection will have to be provided at one of the end caps 32 or 34 for electrically connecting to the electrodes 18 and 20.

Figure 5:
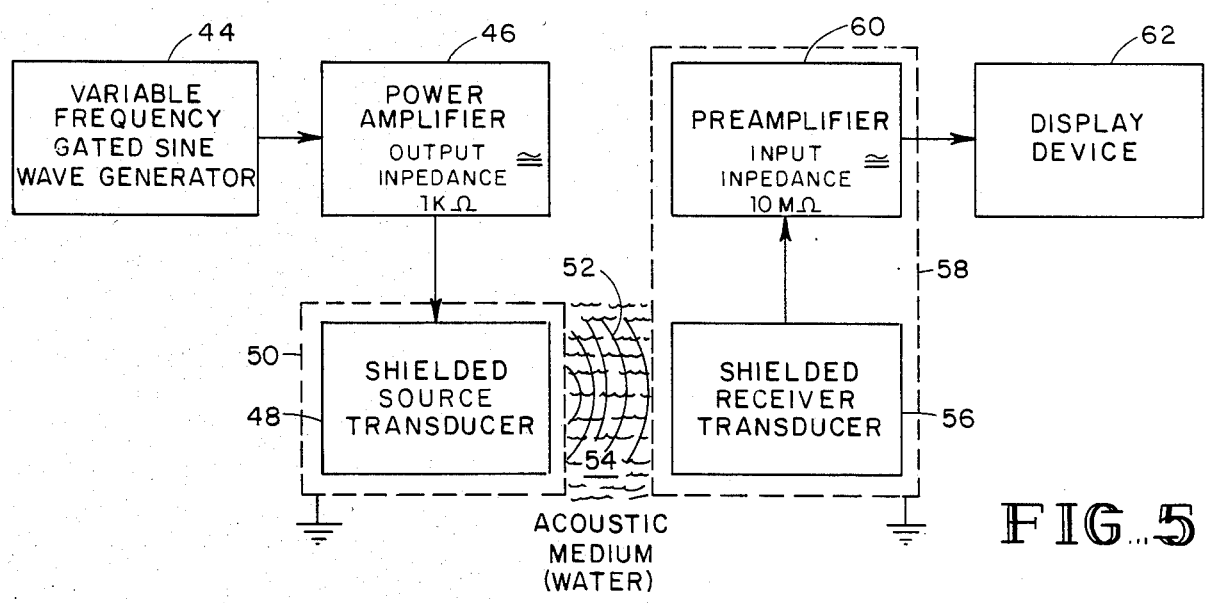
FIG. 5 is an illustrative block diagram of a system utilizing the cylindrical bender-type vibration transducer as both a source and receiver.

Referring now to FIG. 5, a typical block diagram of an acoustical measurement system using a shielded cylindrical bender-type vibration transducer as shown in FIG. 4 is illustrated. A variable frequency gated sine wave generator 44 provides a signal to power amplifier 46. Power amplifier 46 would have a typical output impedance of approximately 1 kilo ohm. In the power amplifier 46, the sine wave from variable frequency gated sine wave generator 44 is amplified and fed to shielded source (or projector) transducer 48. The shielding as is represented by broken lines 50 is actually provided by metallic end caps 32 and 34 and metallic layer 36 as previously described in conjunction with FIG. 4. The vibration of the cylinder walls (as previously described in conjunction with FIG. 4) causes vibrating waves to be transmitted across an acoustical medium 54. A typical such acoustical medium 54 would be water.

The vibrating waves 52 are received by a shielded receiver transducer 56 with the shielding being represented by broken lines 58. Again the shielding 58 could be provided by metallic type end caps 32 and 34 and layer 36 as previously described in conjunction with FIG. 4. Also contained within the shielding 58 is a preamplifier 60 which has a typical input impedance of approximately 10 megohms. The preamplifier 60 amplifies the signal prior to transmission through a suitable connection in one of the end caps 32 or 34 to a suitable display device 62.

One typical arrangement in which applicants have utilized the embodiment as illustrated in FIGS. 4 and 5 has been to measure vibrations in underground formation by creating a disturbance in a bore hole, such as when drilling for an oil well. By proper gating, the reflected waves can be measured to give some idea concerning the characteristics of the underground formation. Another typical embodiment in which a system is shown in FIG. 5 could be used is in underwater detection or transmission of acoustical signals, such as may occur in the ocean or other bodies of water.

In another embodiment of the cylindrical bender-type vibration transducer as shown in FIG. 4, the inner region of the cylindrical bender-type vibration transducer is filled with an incompressible fluid 64. When an excitation signal is applied, the radial contractions and vibrations as illustrated by broken lines 38, cause the incompressible fluid 84 to partially expel from or draw within the cylinder to produce a radiated acoustical wave. Because of the incompressible nature of the fluid 84, the center portions of the end caps 32 and 34 bend in and out in response to the contractions and expansions of the cylinder walls. (The bending of end caps 32 and 34 has not been illustrated in FIG. 4.) By use of this particular configuration, if a vibration was received along the axis of the cylinder, it would cause the end caps 32 or 34 to vibrate in the middle thereof, which vibration would in turn be transmitted to the cylinder walls by the incompressible nature of the fluid 64. This allows an acoustical vibration to be received either radially or along the axis of the cylinder. While the walls of the cylinder do not expand or contract lengthwise, acoustical vibrations will be received through either the end caps 32 or 34 or the cylinder walls with the vibrations being represented by broken lines 38.

Also by sending electrical signals to the transducer, vibrations can be created in an acoustical medium that radiate both radially by the vibrations 38 shown in FIG. 4, and along the axis of a cylindrical transducer 10 by vibration of the end caps 32 and 34 (not shown in FIG. 4).

A comparison of the cylindrical bender-type vibration transducer with other electromechanical transducers may be useful to show the increased sensitivity. For example, a spherical transducer that can be purchased commercially is referred to as EDO-Western Model 6166, which has the following characteristics:
1. Active element—Spherical lead—zirconate—titanate type EC64;
2. Resonance frequency—165 kHz;
3. Impedance at resonance—350 ohms NOM;
4. Capacitance at 1 kHz—3900 picofarads;
5. Cable—15 ft. type 8428;
6. Weight—0.5 oz. in air;
7. Receiving response—— 103 dB re 1 volt/microbar open circuit at 1 kHz to 30 kHz.

In comparison with this spherical transducer, single wall cylinder transducers are available which have the following typical characteristics when embodied in the same dimensions as those of a typical cylindrical bender transducer:
 a. Material—Channelite 5800, Lead-Zirconate-Titanate (commonly referred to as "Navy Type III");
 b. Dimensions—1.75 in. outside diameter, 2.00 in. length, 0.09 in. wall thickness The receiving response for an end capped cylinder can be calculated by the following expression:

$$M_o = 3/2 b\, g_{31}$$

where
 $M_o$ = voltage response of transducer to force in volts/Newtons per unit area
and;

$$b = \tfrac{1}{2}(1-\beta)$$

where
 $\beta$ = inside diameter to outside diameter ratio; and
 $g_{31}$ = piezoelectric constant in volt-meters/Newton.
For Lead-Zirconate-Titanate, Type Channelite 5800,
 $g_{31} = -11.1 \times 10^3$ volt meters/Newton; and for transducer geometry,
 $b = 2.5 \times 10^{-2}$; and
 $M_o = 3/2\, (2.5 \times 10^{-2})(-11.1 \times 10^{-3})$
 $M_o = 4.2 \times 10^{-4}$ volts/Newton/M$^2$
 1 microbar = 0.1 N/M$^2$ so
 $M_o = 4.2 \times 10^{-5}$ volt/microbar = $-88$ dB re 1 volt/microbar Experimental calibration tests on a cylindrical bender-type transducer having the same dimensions as used in the single-wall cylinder calculation shown above resulted in an amplitude sensitivity of $-68$ dB re 1 volt/microbar.

Figure 6:
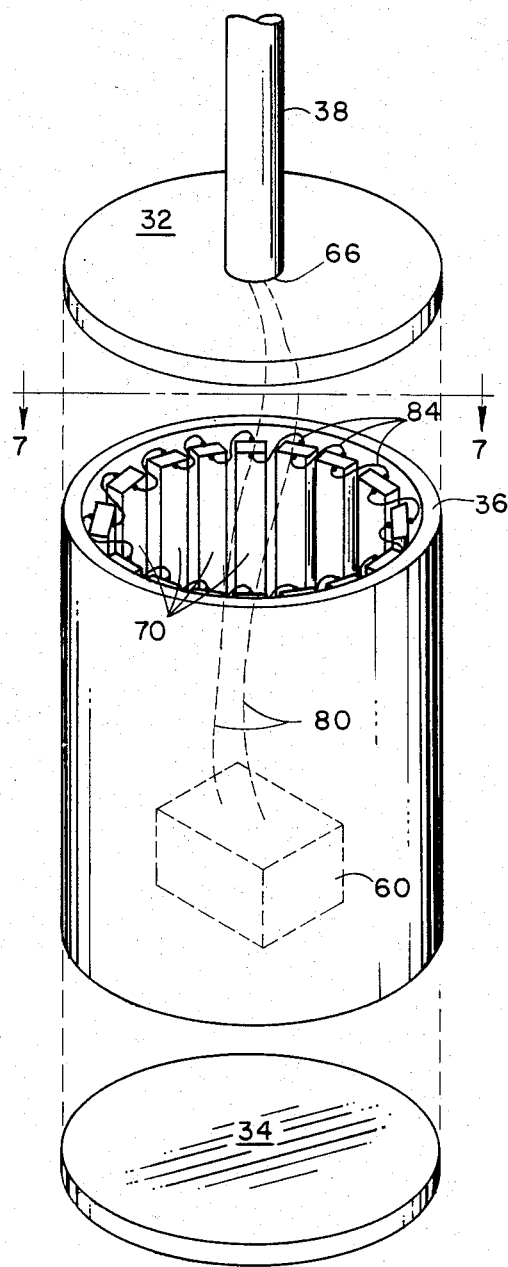
FIG. 6 is an exploded perspective view of an alternative embodiment of a cylindrical bender-type vibration transducer using a barrel stave type of arrangement for the piezoelectric material with the transducer being in a receiver mode of operation.
Figure 7:
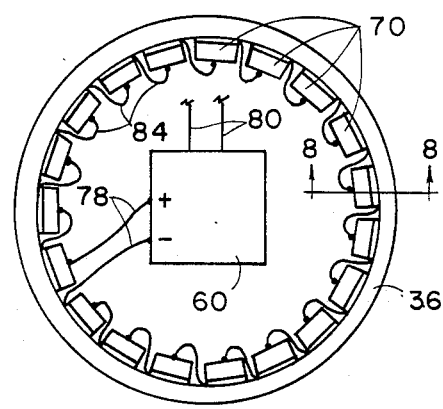
FIG. 7 is a cross-sectional view of FIG. 6 along section lines 7—7.
Figure 8:
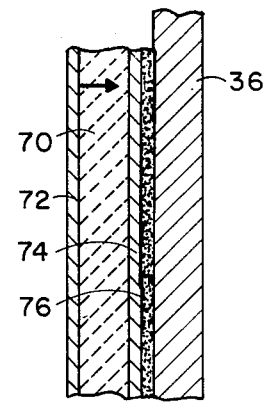
FIG. 8 is an enlarged partial cross-sectional view of FIG. 7 along section lines 8—8.

Referring now to FIGS. 6, 7 and 8 in combination, a modified version of the ceramic cylinder bender-type vibration transducer 10 is illustrated. The outer layer of metallic material 36 and the end caps 32 and 34 remain the same as previously explained in conjunction with FIG. 4. Note that end cap 32 has a suitable shielded opening 66 through which electrical connections are made from the cable 38. However, the inner layer 12 of ceramic material as previously described in connection with FIGS. 1-4 has now been replaced with piezoelectric ceramic strips 70, which are arranged in a barrel stave type of arrangement. Referring to FIG. 8 in combination with FIGS. 6 and 7, an enlarged cross-sectional view of one of the barrel staves and the cylindrical wall is illustrated. The piezoelectric ceramic strip 70 is polarized in the direction represented by the arrow in FIG. 8. Electrodes 72 and 74 are deposited on either side of the piezoelectric ceramic strip 70. The piezoelectric ceramic strip 70 along with the electrodes 72 and 74 is bonded to the metallic layer 36 by a nonconductive bonding agent 76. The thickness of the electrodes 72 and 74 and bonding agent 76 have been exaggerated for illustration purposes.

Referring back to FIGS. 6 and 7 in combination, the manner of connection of the electrodes 72 and 74 of the respective piezoelectric strip 70 is illustrated. The preamplifier 60 (previously described in conjunction with FIG. 5) is connected to two of the electrodes 72 and 74 by leads 78. The connection between the separate electrodes 72 or 74 of the separate piezoelectric ceramic strips 70 is pictorially illustrated in FIGS. 6 and 7 so that each of the piezoelectric ceramic strips 70 and their respective electrodes 72 and 74 are connected in a series connection by leads 84. The preamplifier 60 connects to cable 38 by leads 80.

The configuration shown in FIGS. 6 and 7 is ideally suited as a transducer that receives acoustical signals. By the series connection, a high electrical input impedance is established together with a higher voltage sensitivity for the signals received, such as vibrating waves 52 illustrated in FIG. 5. The higher voltage sensitivity is more desirable for a receiver transducer.

Figure 9:
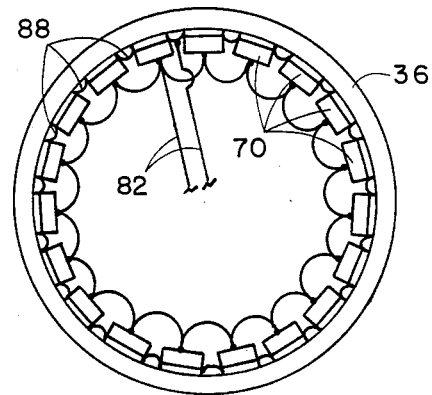
FIG. 9 is a cross-sectional view of FIG. 6 similar to the cross-sectional view as shown in FIG. 7; however, illustrating electrical connections for a projector mode of operation.

Referring to FIG. 9, the same type of barrel stave cylindrical bender-type vibration transducer is shown as was previously explained in connection with FIGS. 6-8, except the connection of the piezoelectric ceramic strips has now been changed to a parallel arrangement by leads 86 and 88 and the preamplifier removed. Notice that the parallel arrangement is again connected to an outside cable through leads 82. The embodiment as shown in FIG. 9 would be a shielded projector transducer as pictorially represented by reference numeral 48 with the shielding being by reference numeral 50 in FIG. 5. The connection as shown in FIG. 9, which is a parallel arrangement, is more desirable for a source transducer because of its low electrical impedance.

In applying many electromechanical transducers, it is desirable to match the mechanical impedance of the transducer with the mechanical impedance of the acoustical medium in which the acoustical signal is being transmitted. It is also desirable to match the electrical impedance of the transducers with the impedances of their respective excitation and receiving circuits. By the use of the configuration as described hereinabove, and particularly the barrel stave arrangement as shown in FIGS. 6-9, both the mechanical and electrical impedances of a cylindrical bender-type transducer can be designed to match a variety of acoustical media while also specifying a given mechanical resonance frequency. Any combination of parallel or series connections can be used to match the electrical impedance of the electrical circuits. Methods of mechanical impedance matching can be utilized, such as using thicker, longer, or different materials for the cylindrical bender-type vibration transducer. When the mechanical impedance of the source transducer is matched to that of the medium, maximum efficiency and energy transfer is achieved.

Another alternative embodiment of the barrel stave type of arrangement explained in connection with FIGS. 6-9 includes the utilization of a much longer external cylinder. The piezoelectric ceramic strips may either be uniformly arrayed as illustrated in FIG. 6 with several arrays extending the full length of the longer external cylinder, or may be staggered around the longer cylinder with piezoelectric ceramic strips butting end-to-end until the internal portion of the cylinder is fully covered with the barrel stave type of arrangement.

In a final alternative embodiment of the present invention, a series of cylinders (without end caps 32 and 34) may be arranged in a cascade arrangement, or a single cylinder with the barrel stave type of arrangement being cascaded in a lengthwise direction. In such an arrangement by use of restrictive orifices at one end thereof, a vibration can be started at one end of the cascade arrangement and by proper timing of subsequent vibrations along the elongated cylindrical bender-type vibration transducer, fluids can be pumped along the elongated cylinder. This is particularly useful in the pumping of biological fluids, such as blood, where it is preferred not to strike the biological fluid with impellers or pistons to obtain the pumping action. By proper timing, the wave sequence as created by one end of the cascade arrangement is moved down the entire length of the elongated cylinder with subsequent waves being likewise propagated in a pumping type of action.

I claim:
1. An electromechanical transducer comprising:
a hollow cylinder with walls formed of a first and a second layer, at least one of said first or second layers being a piezoelectric material polarized in a thickness dimension to cause said piezoelectric material to extend or contract in a longitudinal direction upon electrical signals being applied thereto;
metal electrodes bonded to inside and outside faces of said piezoelectric material, said first layer being rigidly bonded to said second layer by a bonding agent;
means for connecting to said metal electrodes to receive or transmit said electrical signals, when said metal electrodes receive said electrical signals said piezoelectric material will extend or contract in a longitudinal direction to cause symmetrical vibrations of said hollow cylinder only in a radial direction with respect to a longitudinal axis of said hollow cylinder, and when acoustical signals are received said acoustical signals symmetrically vibrate said hollow cylinder in a radial direction to cause said piezoelectric material to extend or contract in a longitudinal direction so that said piezoelectric material generates said electrical signals as transmitted by said metal electrodes;
said first and second layers being sized to give approximately maximum electrical signals or acoustical signals, nodes and anti-nodes being formed by said symmetrical vibrations; and
said symmetrical vibrations being caused by said rigid bonding between said first layer and said second layer and differences in said longitudinal extensions or contractions thereof.

2. The electromechanical transducer as recited in claim 1 further comprising end caps bonded on each end of said hollow cylinder, said end caps moving nodes of said vibration toward each of said end caps.

3. The electromechanical transducer as recited in claim 1 wherein at least one of said first and second layers is a metallic material, said metallic material being outside said piezoelectric material, said bonding between said first and second layers being of an electrically nonconductive bonding agent to prevent current flow therebetween.

4. The electromechanical transducer as recited in claim 2 wherein said transducer is filled with a relatively incompressible fluid so that acoustical signals received on said end caps cause said end caps to vibrate along said axis which in turn causes said walls of said cylinder to symmetrically vibrate radially with respect to said axis or vice versa.

5. The electromechanical transducer as recited in claim 4 wherein said mechanical impedance is adjustable by adjusting thickness or length to match an acoustic radiation impedance of a propagation medium to maximize energy coupling efficiency and operating band width.

6. The electromechanical transducer as recited in claim 1 wherein a series of transducer elements are in an abutting relationship along a center axis with a fluid located therein, said series of transducers being in a cascade arrangement and timed to create wave motion therein to pump said fluid therethrough with rhythmic wave-like motion by contractions and dilations of said series of transducers.

7. The electromechanical transducer as recited in claim 1, 2 or 3 wherein said piezoelectric material is segmented in a barrel stave type of arrangement with each said segment being bonded to an outer of said first and second layers of said hollow cylinder, each said segment having separate said metal electrodes bonded on said inside and outside faces of said piezoelectric material.

8. The electromechanical transducer as recited in claim 7 wherein each segment of piezoelectric material is wired in parallel by said connecting means for maximum efficiency as a source transducer.

9. The electromechanical transducer as recited in claim 7 wherein each said segment of piezoelectric material is wired in series by said connecting means for maximum efficiency as a receiver.

10. The electromechanical transducer as recited in claim 7 wherein said connection means may be wired in any of several ways to match the electrical impedance thereof with electrical impedance of source or receiver circuits.

11. The electromechanical transducer as recited in claim 1, 2 or 3, wherein said first and second layers may be designed in thickness, length, diameter, and material to match mechanical impedance thereof with mechanical impedance of an acoustic medium.

12. The electromechanical transducer as recited in claim 7 wherein said outer of said first and second layers is an electrically conductive metal and end caps bonded on each end of said hollow cylinder are an electrically conductive metal, said end caps being electrically connected to said outer layer to shield inside of said hollow cylinder.

13. The electromechanical transducer as recited in claim 7 wherein said outer of said first and second layers of said hollow cylinder is longer than individual said segments, said segments being abutting end-to-end to extend essentially along the full length of said hollow cylinder.

14. An electromechanical transducer comprising:
a hollow cylinder with walls formed of a first and a second layer, said first and second layers being piezoelectric material polarized in a thickness dimension to cause said piezoelectric material to expand or contract in a longitudinal direction upon electrical signals being applied thereto;
metal electrodes bonded to inside and outside faces of said piezoelectric material, said first layer being rigidly bonded to said second layer by a bonding agent;
means for connecting to said metal electrodes to receive or transmit said electrical signals, when said metal electrodes receive said electrical signals said piezoelectric material symmetrically vibrates said hollow cylinder only in a radial direction with respect to a longitudinal axis of said hollow cylinder, and when acoustical signals are received said acoustical signals symmetrically vibrate said hollow cylinder in a radial direction so that said piezoelectric material generates said electrical signals as transmitted by said metal electrodes;
said metal electrodes being on said inside face of said hollow cylinder and said outside face of said hollow cylinder, said polarization of said first and second layers being in opposite radial directions with electrical connections to said metal electrodes forming a series electrical arrangement suitable for operation as a receiving transducer;
said symmetrical vibrations being caused by said rigid bonding between said first layer and said second layer and differences in said longitudinal expansions or contractions thereof.

15. An electromechanical transducer comprising:
a hollow cylinder with walls formed of a first and a second layer, said first and second layers being piezoelectric material polarized in a thickness dimension to cause said piezoelectric material to expand or contract in a longitudinal direction upon electrical signals being applied thereto;
metal electrodes bonded to inside and outside faces of said piezoelectric material, said first layer being rigidly bonded to said second layer by a bonding agent;
means for connecting to said metal electrodes to receive or transmit said electrical signals, when said metal electrodes receive said electrical signals said piezoelectric material symmetrically vibrates said hollow cylinder only in a radial direction with respect to a longitudinal axis of said hollow cylinder, and when acoustical signals are received said acoustical signals symmetrically vibrate said hollow cylinder in a radial direction so that said piezoelectric material generates said electrical signals as transmitted by said metal electrodes;
said metal electrodes being on said inside face of said hollow cylinder and said outside face of said hollow cylinder and between said layers said polarization of said first and second layers being in same radial direction, one electrical connection to said metal electrode located between said layers and another electrical connection to said metal electrodes inside and outside said layers to form a parallel electrical arrangement suitable for operation as a source transducer;
said symmetrical vibrations being caused by said rigid bonding between said first layer and said second layer and differences in said longitudinal expansions or contractions thereof.

* * * * *